United States Patent [19]

Miyazawa et al.

[11] Patent Number: 4,966,994
[45] Date of Patent: Oct. 30, 1990

[54] METHOD FOR PURIFYING L-GLUTAMINE

[75] Inventors: Masashi Miyazawa; Toyokazu Kaneko; Tetsuya Kaneko; Kenichi Yarita, all of Kawasaki, Japan

[73] Assignee: Ajinomoto Company, Ltd., Tokyo, Japan

[21] Appl. No.: 378,042

[22] Filed: Jul. 11, 1989

[30] Foreign Application Priority Data

Jul. 11, 1988 [JP] Japan .................................. 63-170962

[51] Int. Cl.$^5$ ........................................... C07C 227/00
[52] U.S. Cl. .................................................. 562/554
[58] Field of Search ......................... 562/554; 435/110

[56] References Cited

U.S. PATENT DOCUMENTS 3,206,506  9/1965  Griffith ................................. 562/554
3,886,039  5/1975  Yoshinaga ............................ 435/110

Primary Examiner—Michael L. Shippen
Attorney, Agent, or Firm—Oblon, Spivak, McClelland, Maier & Neustadt

[57] ABSTRACT

L-glutamine is purified by concentrating a fermentation liquor containing at least 40 g/l or more of L-glutamine, or a solution obtained therefrom by filtering off microbial cells, at pH 5.6±0.5, or by cooling the fermentation liquor or the solution after concentration or without concentration at a temperature in the range of 2° to 30° C., thereby giving a slurry of L-glutamine crystals of 70 g/l or higher concentration; (2) separating the crystals from the mother liquor and then dissolving the separated crystals in a water; and (3) bringing the solution thus obtained into contact with an OH-type anion-exchange resin, thereby removing impurities through adsorption.

5 Claims, No Drawings

METHOD FOR PURIFYING L-GLUTAMINE

BACKGROUND OF THE INVENTION

1. Field of the Invention

The present invention relates to a method for purifying L-glutamine (L-Gln) which is used as a starting material for medicinal agents and for other purposes.

2. Description of the Background

L-glutamine can be prepared by organic synthesis, but its synthesis by fermentation has advanced in recent years, producing the compound in high efficiency. L-glutamine tends to undergo decomposition under certain temperature and pH conditions to form pyrrolidonecarboxylic acid (PCA), and once PCA is formed, it is practically impossible to restore L-glutamine from this decomposition product. Hence, scrupulous care must be taken in purifying this compound.

The so-called "resin-treatment process" has been generally used for isolating L-glutamine from its fermentation liquor, in which the liquor is directly, or after removal of microbial cells by a separator of centrifugal or filtration type, brought into contact with a strongly acidic cation-exchange resin to adsorb L-glutamine, followed by elution with an alkaline solution and crystallization. This is an excellent process for isolating and purifying L-glutamine because most of the impurities contained in its fermentation liquor, such as foreign amino acids, PCA (a decomposition product of L-glutamine), microbial cells, soluble proteins, inorganic salts and sugars left unconsumed, can be removed unadsorbed.

The conventional process, however, has problems, which are industrially quite significant, which are that much water is necessary for reactivation and washing of the ion-exchange resin, imposing a big burden for waste water treatment, and that chemical decomposition of L-glutamine is likely to occur as a result of its contact with acids and alkalis in resin treatment resulting in a low recovery rate from the fermentation liquor. A need therefore continues to exist for an improved method of purifying L-glutamine.

SUMMARY OF THE INVENTION

Accordingly, one object of the present invention is to achieve a higher recovery rate of high quality L-glutamine from the fermentation liquor and at the same time alleviate the burden of waste water treatment in L-glutamine production.

Briefly, this object and other objects of the present invention as hereinafter will become more readily apparent can be attained in a method for purifying L-glutamine by concentrating a fermentation liquor containing at least 40 g-l or more of L-glutamine, or a solution obtained therefrom by filtering off microbial cells, at pH 5.6±0.5, or cooling the fermentation liquor or the solution after concentration or without concentration at a temperature in the range of 2° to 30° C., thereby giving a slurry of L-glutamine crystals of 70 g/l or higher concentration; (2) separating the crystals from the mother liquor and then dissolving the separated crystals in a water; and (3) bringing the solution thus obtained into contact with an OH-type anion-exchange resin, thereby removing impurities through adsorption.

DETAILED DESCRIPTION OF THE PREFERRED EMBODIMENTS

The fermentation liquor employed in the method of the present invention must contain 40 g/l or mor of L-glutamine accumulated therein. Use of a liquor containing less than 40 g/l L-glutamine is less practical because of the low crystallization rate and the low plurality of the crystals which form. Prior to crystallization, the fermentation liquor may be subjected to any pretreatment which for all practical purposes does not result in any removal of L-glutamine from the liquor, such as, for example, the removal of microbial cells.

The fermentation liquor, or a solution obtained by the filtration and separation of microbial cells, therefrom, is concentrated or cooled at pH 5.6±0.5 to crystallize out L-glutamine. pH adjustment is conducted by addition of an acid such as hydrochloric acid, because the pH value of the fermentation liquor is generally about 7.0. Preferably, the pH adjustment is carried out prior to concentration or cooling, but it may be done during concentration or cooling when required. Concentration is continued until the content of L-glutamine reaches a level of 70 g/l or higher that ensures a suitable crystallization rate, and hence this operation is unnecessary in some cases when fermentation liquor contains 70 g/l or more of L-glutamine. On the other hand, crystallization by cooling is conducted at a suitable temperature in the range of 2° to 30° C., which may vary with the properties of the fermentation liquor being treated, the predetermined crystallization rate of other factors. Crystallization by cooling is not conducted in some cases, depending on the properties of fermentation liquor, or when using equipment capable of continuous concentration and separation of the crystals which form. A suitable crystallization rate means crystallization at a level which results in crystals, which, when treated with an anion-exchange resin and then purified by commonly used techniques, show a predetermined purity. This value may vary with the properties of fermentation liquor being treated, the intended purity level of final products, the type of crystallizer and other equipment used, crystallization conditions and other factors.

The slurry obtained by crystallization is separated into crystals and mother liquor, and the crystals are normally washed one to several times with a small amount of water. The solid-liquid separator used in the step may be a centrifuge of the batch or continuous type.

The collected crystals are brought into contact with an OH-type anion-exchange resin in the form of an aqueous solution. The resin used may be a strongly basic anion-exchange resin such as IRA-430 and IRA-904 of Rohm & Hass, and PA-416 and SA-21A of Mitsubishi Chemical Industries, or a moderately or weakly basic anion-exchange resin such as IRA-35, IRA-45, IRA-68 and IRA-93 of Rohm & Haas, and WA-10, WA-21 and WA-30 of Mitsubishi Chemical Industries, but the latter type is preferred. A suitable amount of resin is used such that required amounts of impurities in the solution of crystals can be removed, which amount depends on the intended purity of final products. This amount may be determined by taking, as an index, a proper type of impurity such as glutamic acid and PCA. The resin may be used by mixing it with a solution of L-glutamine in a bath, but use of the commonly employed column system, both single-column and multi-column systems, ensures more simple opertion.

In order to minimize the decomposition of L-glutamine, the aqueous solution is preferably brought into contact with the resin at a temperature of about 0° to 40° C. and at a pH of about 5.6±0.5.

The aqueous solution of L-glutamine from which impurities have been removed by contact with an anion-exchange resin is then further purified by the usual methods, for example, decolorization with activated charcoal or the like, followed by concentration, as required, and crystallization by cooling, thus giving final products.

The mother liquor remaining after the crystals of L-glutamine have been recovered from its fermentation liquor by concentration or cooling still contains L-glutamine in an amount corresponding to its solubility in water, in addition to impurities such as L-glutamic acid, PCA, microbial cells, soluble proteins, inorganic salts and sugars. It is therefore desirable to recover the L-glutamine left in the mother liquor to enhance its recovery rate. This recovery can be effected by first removing polymeric substances which inhibit crystal growth such as soluble proteins and microbial cells by the ultrafiltration (UF) membrane technique, and then isolating l-glutamine crystals by the usual methods such as crystallization by concentration or cooling. The crystals thus obtained are purified by treatment with an anion-exchange resin in the same way as described above, either alone or in combination with the crystals separated above from the fermentation liquor through crystallization by concentration or cooling. Thus, removal of crystal-growth inhibiting substances from the mother liquor enables isolation of high-purity L-glutamine crystals and enhances the total yield of the final products, thus providing a purification method of high practical utility.

The "direct crystallization process", in which crystals of L-Gln are directly recovered from their fermentation liquor without any pretreatment, generally gives crystals of lower purity compared with the "resin-treatment process". Hence, establishing a method of effectively purifying low-purity crystals of L-glutamine is an essential factor to make the "direct crystallization process" sufficiently practical.

As a result of various studies on the impurities in low-purity L-glutamine obtained from its fermentation liquor through crystallization by concentration or cooling, it has been found that foreign amino acids (fermentaion by-products), PCA (a decomposition product of L-glutamine), inorganic salts, proteins and sugars are major components of the impurities. Further intensive studies on how to remove these impurities have established an effective purification method using anion-exchange resins. L-glutamine of low purity has hitherto been purified by recrystallization. In this conventional method, L-glutamic acid and PCA tend to be incorporated in recrystallized products, and hence recrystallization must be repeated to obtain high-purity products, thus making its practical application most impossible in terms of cost. In the method of the present invention, in contrast, L-glutamic acid and PCA, as well as inorganic salts, can be completely removed by adsorption on an anion-exchange resin, significantly enhancing the quality of the facial product. The problems involved in the "direct crystallization method" can thus be solved completely by the purification technique of the present invention.

Having generally described this invention, a further understanding can be obtained by reference to certain specific examples which are provided herein for purposes of illustration only and are not intended to be limited unless otherwise specified.

EXAMPLE 1

Fifty liters of a fermentation liquor containing 42 g/l L-Gln was adjusted to pH 5.6 by addition of 35%-HCL, was concentrated to a connection of 120 g/l and then cooled to 5° C. at a rate of 5° C./hr to effect crystallization. L-Gln crystals (No. 1) which formed were separated from the slurry having a mother liquor containing microbial cells and other impurities. Separation was accomplished in a superdecanter P4Y.

The separated mother liquor (48 liters) was heated and filtered through a hollow-fiber UF membrane (nominal limit M.W.: 6000) to remove microbial cells and other impurities, and the transparent filtrate thus obtained was concentrated to effect crystallization (final L-Gln concentration: 230 g/l).

The concentration slurry was transferred to a crystallizer, cooled with stirring from 45° C. down to 20° C., and placed into a basket-type centrifugal separator to remove mother liquor. The crystal cake collected in the basket was washed with water in an amount of about 40% of its weight, giving L-Gln crystals (No. 2).

The amounts of L-glutamine recovered (No. 1 and No. 2) were 1.2 Kg and 0.6 Kg, respectively, and the total recovery rate from the fermentation liquor amounted to 85.7%.

A mixture of 0.6 Kg L-Gln No. 1 crystals and 0.3 Kg No. 2 crystals was dissolved in water by heating to 40° C., thereby preparing an aqueous solution containing 40 g/l L/Gln (pH 4.8). This solution was allowed to pass through a column packed with 0.5 liter of Amberlite IRA-68 [OH]-resin (a moderately basic anion-exchange) to remove L-glutamic acid (L-Glu), PCA, sulfate and other impurities by adsorption. The withdrawn solution was decolorized with 45 g activated charcoal at 40° C., the decolorized solution was filtered through a suction filter, the filtrate (23 liters) was concentrated to effect crystallization, and the resulting slurry was cooled, giving 0.8 Kg of L-Gln pure cyrstals (A recovery rate from the fermentation liquor of 76%.)

The contents of impurities in the L-Gln crystals obtained at the respective purification stages are shown in the table below.

|  | Glu/Gln | PCA/Gln | $SO_4^{--}$/Gln | Microbial-cell protein |
| --- | --- | --- | --- | --- |
| L-Gln crystals (No. 1) | 0.4% | 0.7% | 0.6% | 0.2% |
| L-Gln crystals (No. 2) | 1.3% | 1.7% | 1.5% | (±) |
| L-Gln pure crystals | 0.005% | 0.002% | 0.005% | (−) |

EXAMPLE 2

Fifty liters of a fermentation liquor containing 74 g/l L/Gln was adjusted to pH 5.6 by the addition of 35%-HCl, cooled to 5° C. at a rate of 5° C./hr in a crystallizer fitted with a stirrer, and then matured at 5° C. for four hours to effect crystallization. The slurry thus obtained was treated in a superdecanter P4Y giving L-Gln crystals (No. 1).

The separation mother liquor was treated in the same manner as in Example 1 giving L/Gln crystals (No. 2).

The amounts of L-glutamine recovered (No. 1 and No. 2) were 1.5 Kg and 1.5 Kg, respectively, and the total recovery rate from the fermentation liquor amounted to 83.8%.

A mixture of L/Gln No. 1 crystals and No. 2 crystals was dissolved in water in the same way as in Example 1, the solution was allowed to pass through a column packed with the moderately basic anion-exchange resin, followed by decolorization, concentration and cooling to effect crystallization, giving 2.7 Kg of L-Gln pure crystals (A recovery rate from the fermentation liquor of 73%).

The contents of impurities in L-Gln crystals obtained in respective purification stages are shown in the table below.

|  | Glu/Gln | PCA/Gln | $SO_4^{--}$/Gln | Microbial-cell protein |
|---|---|---|---|---|
| L-Gln crystals (No. 1) | 0.3% | 0.5% | 0.3% | 0.15% |
| L-Gln crystals (No. 2) | 1.5% | 1.9% | 1.7% | (±) |
| L-Gln pure crystals | 0.005% | 0.002% | 0.005% | (−) |

COMPARATIVE EXAMPLE 1

A mixture of 0.6 Kg L-Gln crystals (No. 1) and 0.3 Kg crystals (No. 2), obtained in Example 1, was recrystallized in a usual way as described below. The crystals were dissolved in water to a concentration of 40 g/l, activated charcoal was added to the solution in an amount of 5% based on the weight of L-Gln, and decolorization was conducted by heating at 40° C. After filtering through activated charcoal, the decolorized solution was concentrated to effect crystallization, and the resulting slurry was cooled to 5° C. giving 0.81 Kg of pure crystals (A recovery rate from the fermentation liquor of 77%).

The contents of impurities in L-Gln crystals obtained in the respective purification stages are shown in the table below.

|  | Glu/Gln | PCA/Gln | $SO_4^{--}$/Gln | Microbial-cell protein |
|---|---|---|---|---|
| L-Gln crystals (No. 1) | 0.4% | 0.7% | 0.6% | 0.2% |
| L-Gln crystals (No. 2) | 1.3% | 1.7% | 1.5% | (±) |
| L-Gln pure crystals | 0.34% | 0.1% | 0.01% | (−) |

COMPARATIVE EXAMPLE 2

Fifty liters of a fermentation liquor containing 42 g/l L-Gln were freed from microbial cells using a centrifuge, and the treated solution was adjusted to pH 1.8 and allowed to pass through a column packed with 50 liters of Duolite C-20 (a strongly acidic anion-exchange resin) to adsorb L-Gln on the resin. In this operation, PCA, soluble proteins, inorganic salts, sugars and a portion of the Glu were removed unadsorbed.

After washing the column with water, the adsorbed L-Gln was eluted with 0.5N-NH$_4$OH, the elutant (65 liters) was concentrated to a concentration of 450 g/l, and the resulting slurry was cooled to 5° C. and treated in a basket-type centrifugal separator giving 1.6 Kg of L-Gln crystals (No. 1) (recovery rate: 76%). The mother liquor was further concentrated and cooled, but no crystals of L-Gln were separated. The crystals (No. 1) obtained above were purified by recrystallization in the same way as in Comparative Example 1 affording 1.44 Kg of pure crystals (A recovery rate from the fermentation liquor of 68.6%).

The contents of impurities in L-Gln crystals obtained in the respective purification stages are shown in the table below.

|  | Glu/Gln | PCA/Gln | $SO_4^{--}$/Gln | Microbial-cell protein |
|---|---|---|---|---|
| L-Gln crystals (No. 1) | 0.3% | 0.01% | 0.01% | 0.03% |
| L-Gln pure crystals | 0.12% | 0.002% | 0.002% | (−) |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for purifying L-glutamine which comprises:

(i) concentrating a fermentation liquor containing 40 g/l or more of L-glutamine or a solution obtained therefrom from which microbial cells have been removed, at a pH of 5.6±0.5, thereby giving a slurry of L-glutamine crystals of 70 g/l or higher concentration;

(ii) separating said crystals from the mother liquor and then dissolving the separated crystals in water; and (iii) bringing the water solution of L-glutamine in contact with an OH-type anion-exchange resin, thereby removing any impurities in the water solution by adsorption.

2. The process of claim 1, which further comprises: cooling the concentration liquor of step (i) to a temperature within the range of 2° to 30° C.

3. A method for purifying L-glutamine, which comprises:

(i) cooling a fermentation liquor containing 40 g/l or more of l-glutamine or a solution obtained therefrom from which microbial cells have been removed, at a pH of 5.6±0.5, at a temperature within the range of 2° to 30° C., thereby giving a slurry of L-glutamine crystals of 70 g/l or higher concentration;

(ii) separating said crystals from the mother liquor and then dissolving the separated crystals in water; and (iii) bringing the water solution of L-glutamine in contact with an OH-type anion-exchange resin, thereby removing any impurities in the water solution by adsorption.

4. The method of claim 1 or 3, wherein said OH-type anion-exchange resin is a strongly, moderately or weakly basic anion-exchange resin.

5. The method of claim 1 and 3, wherein the water solution is contacted with said anion-exchange resin at a temperature of about 0° to 40° C. at a pH of 5.6±0.5.

* * * * *